(12) United States Patent
Buchanan

(10) Patent No.: US 8,057,995 B2
(45) Date of Patent: Nov. 15, 2011

(54) METHODS OF CHROMOSOME DRYING AND SPREADING

(75) Inventor: Philip D. Buchanan, Chapel Hill, NC (US)

(73) Assignee: GeneCare Medical Genetics Center, Inc., Chapel Hill, NC (US)

( * ) Notice: Subject to any disclaimer, the term of this patent is extended or adjusted under 35 U.S.C. 154(b) by 582 days.

(21) Appl. No.: 11/545,827

(22) Filed: Oct. 11, 2006

(65) Prior Publication Data
US 2008/0090227 A1    Apr. 17, 2008

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ..... 435/6; 536/23.1, 536/24.3
See application file for complete search history.

(56) References Cited

U.S. PATENT DOCUMENTS

| | | | |
|---|---|---|---|
| 5,851,790 A * | 12/1998 | Walker et al. ............... | 435/40.51 |
| 2001/0016351 A1 * | 8/2001 | Sorge et al. ................. | 435/320.1 |
| 2001/0046682 A1 * | 11/2001 | Lichtenwalter .................... | 435/6 |
| 2005/0042767 A1 * | 2/2005 | Machida et al. .............. | 436/174 |
| 2006/0154263 A1 * | 7/2006 | Vallabhaneni .................... | 435/6 |

OTHER PUBLICATIONS

Preist J.H. Cytogenetics Chapter 4-7 pp. 52-92 Editors French et al. published by Lea & Febiger Philadelphia, PA (1969).*
Boyle et al. Chapter 3 : "The Cytogenetics of pregnancy" in "Human Cytogenetics :constitutional analysis" 3rd Edition; Editor Rooney, D. E.; published by Oxford University Press ; New York, NY (2001).*
Henegariu et al., Improvements in cytogenetic slide preparation : Controlled chromosome spreading, chemical aging and gradual denaturing. Cytometry 43 : 101-109 (2001).*
Zvarich MT, et al., "Automation in the Cytogenetic Laboratory Offers Significant Benefits," *Association of Cytogenetic Technologists, Fifteenth Annual Meeting*, Santa Fe, New Mexico, 1990.
Zvarich, Michael, et al., "Robotic Harvest of Phytohaemagglutinin— Stimulated Peripheral Blood Lymphocyte Cultures," *Association of Cytogenetic Technologists, Fifteenth Annual Meeting*, Sante Fe, New Mexico, 1990.
Buchanan PB, Lab Management and Automated Karyotyping: Seventh Annual Meeting of the Southeastern Regional Genetics Group, Atlanta, GA (1987).
Buchanan PD, Laundon CH: Early Amniocentesis and Computer Assisted Cytogenetics, Seventh Annual Meeting of the Southeastern Regional Genetics Group, Atlanta GA (Mar. 1989).
Buchanan PD, Laundon CH: Lab Management and Automation, Eighth Annual Meeting of the Southeastern Regional Genetics Group, Atlanta GA (1990).
Zvarich MT, et al., "Robotic Harvest of Phytohaemagglutinin— Stimulated Peripheral Blood Lymphocyte Cultures," Southern Genetics Group, Thirteenth Summer Meeting, San Destin, FL (1990).
Zvarich MT, et al., "Robotic Harvest of Blood Cultures," Society of Perinatal Obstetricians, Orlando, Florida (1992).

* cited by examiner

*Primary Examiner* — Ethan Whisenant
(74) *Attorney, Agent, or Firm* — Foley Hoag LLP

(57) ABSTRACT

The present invention provides for a method of drying and spreading chromosomes from various biological samples to yield optimal chromosomal spreading. The method requires preparing a biological sample for treatment, providing a cytogenetic chamber capable of setting predetermined conditions, pre-testing a portion of the biological sample in the cytogenetic chamber, and finally treating the remaining biological sample. The method is useful to yield metaphase chromosomes that are small and rounded, with very few overlapping or scattered chromosomes. Furthermore, the method is uses restricted ranges of temperature and relative humidity to achieve consistent chromosomal spreading. The morphologies of the chromosomes are preserved in order to execute banding techniques at 550 bands and chromosomal analysis on high-resolution chromosomes.

15 Claims, 3 Drawing Sheets

Air Flow Fixed

Chromosome Spread Consistency

Air Flow: Fixed

Chromosome Spread Consistency

Air Flow: Fixed

Chromosome Spread Consistency

Air Flow: Fixed

Chromosome Spread Consistency

Air Flow: Fixed

METHODS OF CHROMOSOME DRYING AND SPREADING

BACKGROUND OF THE INVENTION

1. Field of the Invention

The present invention relates generally to methods of chromosome drying and spreading. Further, the present invention relates to a method of drying chromosomes from various biological samples to yield optimal chromosomal spreading.

2. Description of the Prior Art

With the advent of cytogenetics, the ability to analyze chromosomal material has become increasingly important. Cytogenetic analyses are widely used for peripheral blood studies, hematological malignancy investigations, screening prenatal defects, and solid tissue and solid tumor research. Peripheral blood is often analyzed to detect numerical and structural abnormalities of chromosomes. For less obvious chromosomal abnormalities, such as translocations, deletions, and duplications, chromosomal analysis having higher resolutions and more detailed banding are required. Cytogenetics may also be used for early diagnosis of diseases. In order to successfully conduct cytogenetic studies, it is imperative that the morphology of the chromosomes is accurately preserved during analysis.

Cytogenetic studies have become increasing popular with the development of hypotonic treatments in the 50's, the use of phytohemagglutinin (PHA) to stimulate lymphocyte cultures in the 60's, high resolution banding and robotic harvesting in the 70's and 80's. Ultimately, problems continued to exist with respect to achieving optimal chromosomal drying and spreading for chromosomes of interest. In the past, incubators were used to dry biological samples in order to isolate and spread chromosomes for analysis, however the incubators were often problematic because certain environmental conditions could not be regulated such as relative humidity, temperature, and drying times. U.S. Pat. Nos. 5,976,871 and 5,851,790 disclose a cytogenetic chamber that allows a user to regulate the chamber's environmental conditions by setting a precise conditions based on temperature, relative humidity, air flow and time.

Although cytogenetic chambers are currently available, there is a need for a method that provides for optimal chromosome drying and spreading. The present invention takes into consideration the fact that biological samples, from various subjects to be analyzed, are often limited in quantity and is costly to acquire. Additionally, the present invention provides for a method to achieve optimal chromosomal drying and spreading for various biological samples. While the environmental conditions of the drying chamber are important, equally important are the steps taking in preparing the sample and ensuring that the proper environmental conditions have been actually realized before treating an entire biological sample.

SUMMARY OF THE INVENTION

A first aspect of the present invention is directed to a method for drying and spreading chromosomes. The method provides for preparing a biological sample for treatment. The biological sample is prepared for treatment by obtaining a biological sample of cells, transferring the sample of cells onto a support, harvesting the sample of cells, and then adding a fixative agent to the cells after the cells are harvested. A cytogenetic chamber capable of setting predetermined conditions is provided. The cytogenetic chamber is pre-tested by setting the chamber to a predetermined condition based on the biological sample being treated. A portion of pre-testing cells with the fixative agent are placed into the chamber and the remainder of the cells are reserved to the side. The pre-testing cells in the chamber become acclimated to the predetermined conditions before drying. The fixative from the pre-testing cells is aspirated, and the pre-testing cells are dried until spreading is optimized. The pre-testing cells are removed and analyzed for optimal chromosomal spreading. Finally, the reserved cells are placed into the cytogenetic chamber at the same predetermined conditions used for the pre-testing that resulted in optimal spreading. The reserved cells are acclimated to the predetermined conditions, the fixative is aspired from the reserved cells, and the cells are dried and then analyzed for optimal chromosomal spreading.

A second aspect of the present invention is to provide a method for drying chromosomes. The method provides for preparing a biological sample for treatment. The biological sample is prepared for treatment by obtaining a biological sample of cells from an amniocyte, an early amniocyte, and/or a chorionic villus sample (CVS), transferring the sample of cells onto a support, harvesting the sample of cells, and then adding a fixative agent to the cells after the cells are harvested. A cytogenetic chamber capable of setting predetermined conditions is provided. The cytogenetic chamber is pre-tested by setting the chamber to a predetermined condition of about 30.0-32.0° C. and a relative humidity of about 35-37%. A portion of pre-testing cells with the fixative agent are placed into the chamber and the remainder of the cells are reserved to the side. The pre-testing cells in the chamber become acclimated to the predetermined conditions before drying. The fixative from the pre-testing cells is aspirated, and the pre-testing cells are dried until spreading is optimized. The pre-testing cells are removed and analyzed for optimal chromosomal spreading. Finally, the reserved cells are placed into the cytogenetic chamber at the same predetermined conditions used for the pre-testing that resulted in optimal spreading. The reserved cells are acclimated to the predetermined conditions, the fixative is aspired from the reserved cells, and the cells are dried and then analyzed for optimal chromosomal spreading.

A third aspect of the present invention is to provide a method for drying chromosomes. The method provides for preparing a biological sample for treatment. The biological sample is prepared for treatment by obtaining a biological sample of cells from a product of conception and skin tissue, transferring the sample of cells onto a support, harvesting the sample of cells, and then adding a fixative agent to the cells after the cells are harvested. A cytogenetic chamber capable of setting predetermined conditions is provided. The cytogenetic chamber is pre-tested by setting the chamber to a predetermined condition of about 31.0-33.0° C. and a relative humidity of about 36-38%. A portion of pre-testing cells with the fixative agent are placed into the chamber and the remainder of the cells are reserved to the side. The pre-testing cells in the chamber become acclimated to the predetermined conditions before drying. The fixative from the pre-testing cells is aspirated, and the pre-testing cells are dried until spreading is optimized. The pre-testing cells are removed and analyzed for optimal chromosomal spreading. Finally, the reserved cells are placed into the cytogenetic chamber at the same predetermined conditions used for the pre-testing that resulted in optimal spreading. The reserved cells are acclimated to the predetermined conditions, the fixative is aspired from the reserved cells, and the cells are dried and then analyzed for optimal chromosomal spreading.

A fourth aspect of the present invention is to provide a method for drying chromosomes. The method provides for preparing a biological sample for treatment. The biological sample is prepared for treatment by obtaining a biological sample of cells from a blood specimen, a bone marrow, and a tumor cell, transferring the sample of cells onto a support, harvesting the sample of cells, and then adding a fixative agent to the cells after the cells are harvested. A cytogenetic chamber capable of setting predetermined conditions is provided. The cytogenetic chamber is pre-tested by setting the chamber to a predetermined condition of about 32° C. and a relative humidity of about 36-46%. A portion of pre-testing cells with the fixative agent are placed into the chamber and the remainder of the cells are reserved to the side. The pre-testing cells in the chamber become acclimated to the predetermined conditions before drying. The fixative from the pre-testing cells is aspirated, and the pre-testing cells are dried until spreading is optimized. The pre-testing cells are removed and analyzed for optimal chromosomal spreading. Finally, the reserved cells are placed into the cytogenetic chamber at the same predetermined conditions used for the pre-testing that resulted in optimal spreading. The reserved cells are acclimated to the predetermined conditions, the fixative is aspired from the reserved cells, and the cells are dried and then analyzed for optimal chromosomal spreading.

These and other aspects of the present invention will become apparent to those skilled in the art after a reading of the following description of the preferred embodiment when considered with the drawings, as they support the claimed invention.

DETAILED DESCRIPTION

Figure 1:
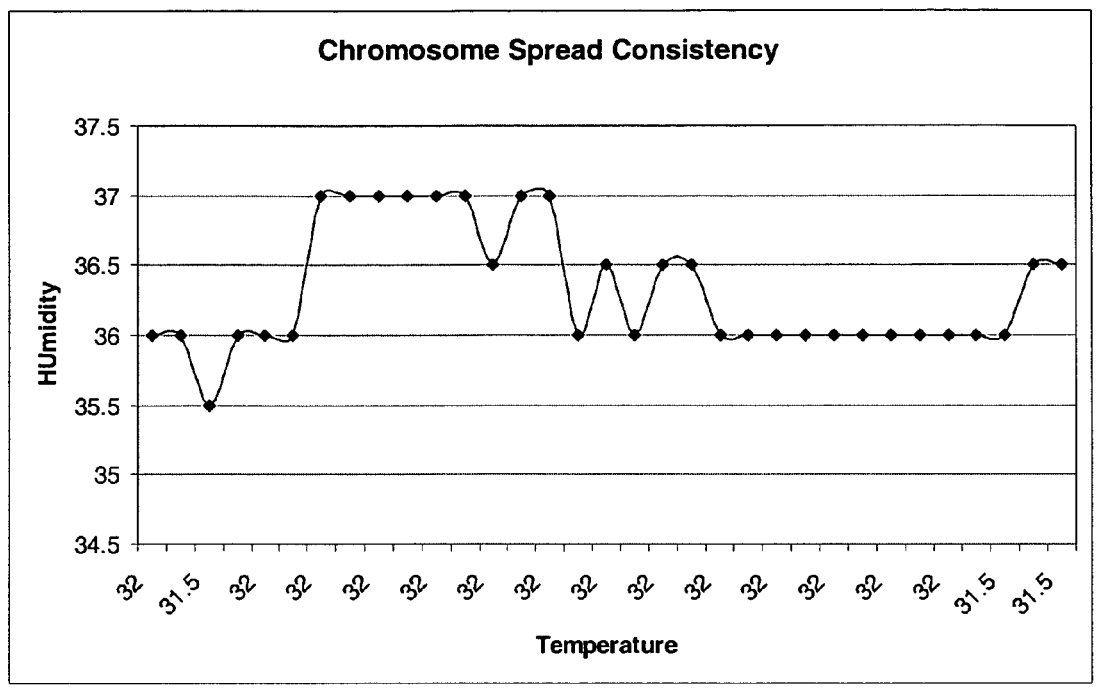
FIG. 1 is a graph showing consistent chromosome spreading based on optimal temperatures (° C.) and relative humidity (%) ranges. This is also shown in FIG. 2d.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto. The present invention relates to an improved method of drying and spreading chromosomes for cytogenetic studies. In the preferred embodiment, a biological sample is prepared for treatment in a cytogenetic chamber. The method of the present invention requires first obtaining a biological sample. The type of abnormality or defect being screened will determine the necessary biological sample. For example, in order to detect prenatal diseases such as chromosomal rearrangement or mosaicism—amniocytes, early amniocytes, or chrorionic villus samples (CVS) may be obtained. If testing for chromosomal abnormalities relating to miscarriages, products of conception tissue may be used. Skin tissue may be used as a viable alternative when peripheral blood is not available in situations where a patient has expired. Chromosomal analyses of blood specimens are vital to detect early stages of certain hematological malignancies such as chronic leukemia or lymphomas. Additionally, tissues relating to solid tumors require chromosomal analysis for early diagnosis, as well as for monitoring the development of a particular disease. Finally, bone marrow is available for karyotyping and detecting aneuploidies. Thus, chromosomal analysis may be conducted on any type of tissue depending on what is being screened. In the preferred embodiment of the present invention, the biological samples may be obtained from the above-mentioned tissues. For some biological samples the tissue culture may need to be performed in incubators with special media depending on the type of tissue. The tissue culture techniques according to the present invention are provided to facilitate cell division and to obtain a larger number of rapidly dividing cells. Preferably, all tissues are grown in culture according to these techniques except for the direct harvest of CVS and bone marrow.

After the desired biological sample is obtained, the sample is prepared to be dried and spread in the cytogenetic chamber. First, the cell sample is transferred onto a support such as slide or cover slip. The cell sample is then harvested in an automatic harvester. In the preferred embodiment a TECAN™ robotic automatic harvester is used according to standard practices. Harvesting ensures that the tissue sample containing the cells of interest are properly isolated and then processed to create a solution of viable cells.

After harvesting, a fixative agent is added to the harvested cells. The fixative agent is used to preserve the integrity of the cell morphology, and more specifically the histological detail of the cell is preserved which is crucial for chromosomal analysis. It has been found that the stronger the fixture, the better the cellular morphology is preserved, however the cells become less accessible. Therefore, it is important to use a fixative having an appropriate concentration that will optimize the chromosome drying methods of the present invention. While any number of fixative agents known in the art may be used, in the preferred embodiment of the present invention, about 2 mL of a fixative agent having a 3:1 ratio of methanol to glacial acetic acid are added for optimal results. In developing the methods of the present invention, different ratios of the same compound were tested to provide the optimum fixtature agent ratio. While it is known in the art that acetic acid attracts water and automatically dilutes itself, it is preferred for the methods of the present invention to use glacial acetic and methanol to ensure that no water is present for optimal results. Once the fixative agent is added, the fixative-treated cells are ready to be dried in the cytogenetic chamber.

The speed of drying and the environmental conditions in the drying chamber directly affect chromosome spreading. During the drying process, the fixative evaporates and the cell spreads by becoming thinner and wider. In order to achieve optimal spreading, the cells must not be dried too fast or too slow. The present invention defines optimal spreading when the cell membranes are ruptured and the chromosomes are spread out in small rounded metaphase areas with few overlapping chromosomes, without chromosomal breakage, without fuzzy edges, without any cytoplasm remaining, and without over spreading or scattering. If the cells are dried too fast, the cells will not spread and the chromosomes will remain compact and overlapped. If the cells are dried to slow, the cells will spread too much causing the chromosomes to break and scatter. Accordingly the present invention requires a cytogenetic chamber, or drying chamber, that can be programmed to have specific predetermined conditions to control the rate of drying, such as temperature, relative humidity, and flow rates. Thermotron® is a company that offers one type of cytogenetic drying chamber that can be set according to predetermined conditions.

Often times the biological tissue samples to be dried and spread are not available in large quantities and require expensive procedures to obtain, such as amniocytes or CVS. Accordingly, it is important that the drying conditions in the chamber are accurate otherwise the valuable samples can be destroyed without being properly analyzed. In order to prevent loss of the entire biological specimen, the preferred embodiment of the present invention requires pre-testing the cytogenetic chamber with a portion of the prepared biological sample. In the preferred embodiment, a portion of the fixative-treated cells are pre-tested in the cytogenetic chamber, while the remaining fixative-treated cells are reserved on the side for drying after pre-testing of the drying chamber is complete. The present invention refers to the cells used for pre-testing as pre-testing cells, and the remaining cells as the reserved cells.

As mentioned above, the actual environmental conditions of the drying chamber are critical. The present invention has found that different biological samples require specific environmental conditions to achieve optimal chromosomal spreading and drying. For example, in the preferred embodiment amnioctyes, early amniocytes, and chorionic villus samples (CVS) achieve optimal chromosomal spreading at about 30.0-32.0° C. and a relative humidity of about 35-37%. In one embodiment, the present invention reaches optimal chromosomal spreading at 31.5° C. and 36.5% relative humidity for amnioctyes, early amniocytes, and CVS. For products of conception and skin tissue, the preferred embodiment reaches optimal chromosomal spreading at about 31.0-33.0° C. and a relative humidity of about 36-38%. For blood specimens, a bone marrow, and a tumor cells, the preferred embodiment realizes optimal chromosomal drying and spreading at about 32° C. and a relative humidity of about 36-46%. The specific temperature and relative humidity for realizing optimal chromosomal drying and spreading is for each type of biological sample is defined as the predetermined condition. As observed above, the predetermined condition will vary depending on the biological sample being treated. While other ranges in the prior art may be used, they are not preferred for the methods of the present invention to provide optimal results.

After the environmental condition is established for the specific biological sample, the cytogenetic chamber is set with the predetermined conditions. The preferred embodiment of the present invention suggests running the cytogenetic chamber for about 1-1½ hours at the predetermined conditions in order for the chamber to equilibrate to the specific environmental conditions.

Figure 2A:
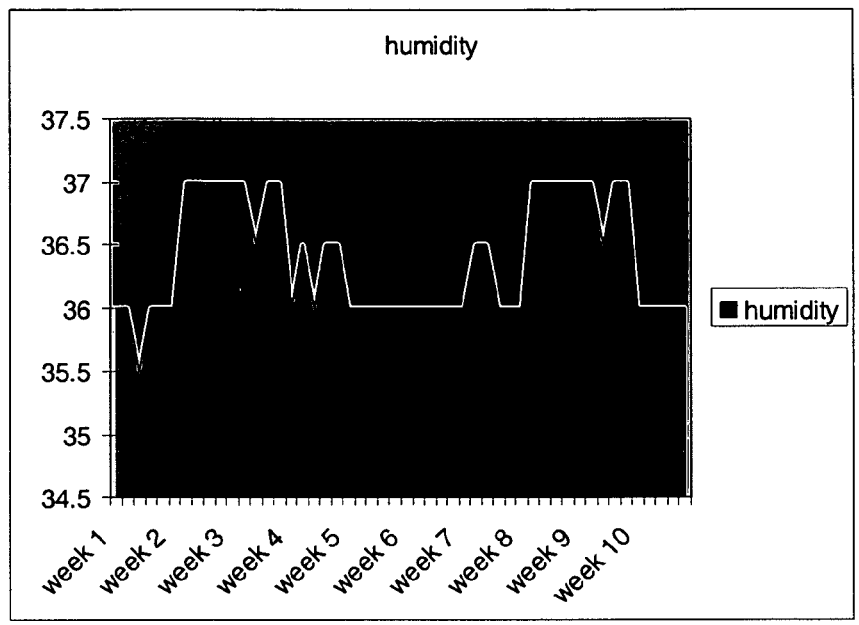
FIGS. 2a, 2b, and 2c are graphs showing testing of consistent chromosome spreading based on optimal temperatures (° C.) and relative humidity (%) ranges testing over a 10 week period for which the air flow is fixed.
Figure 2B:
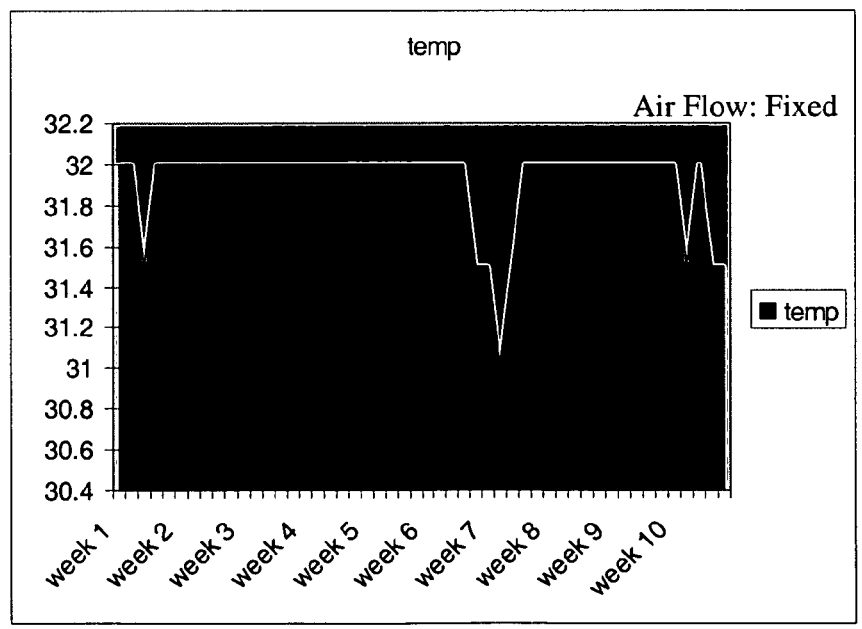
Figure 2C:
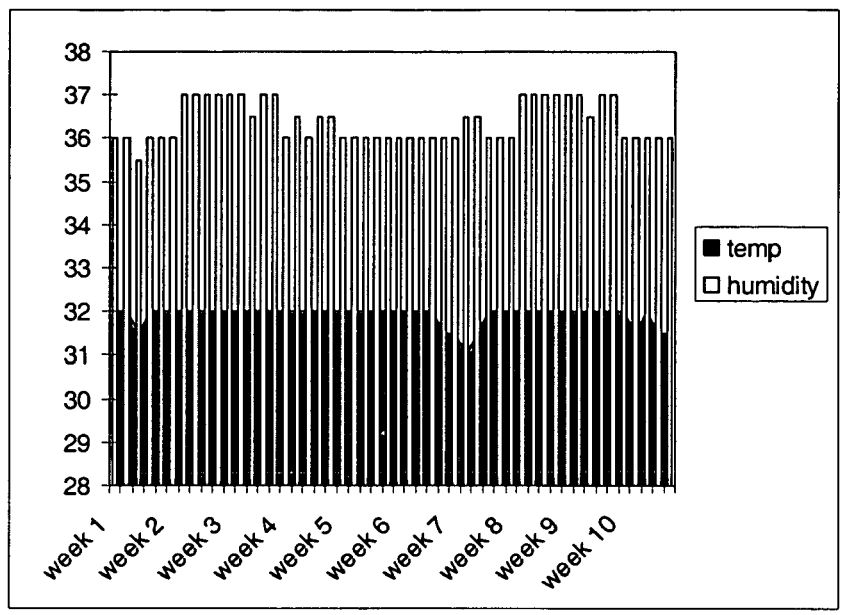
Figure 2D:
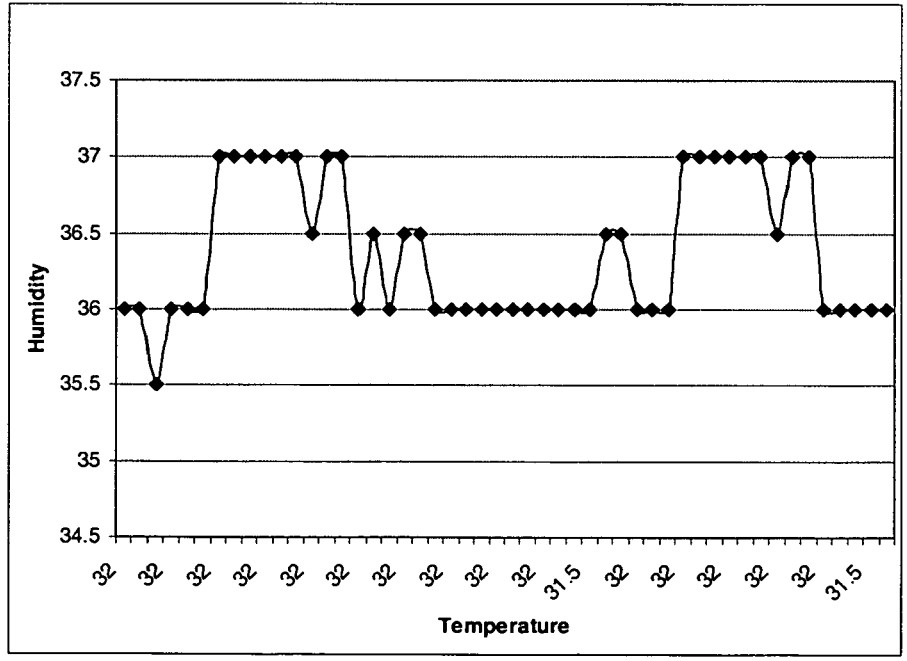

After the cytogenetic chamber has been running at the predetermined condition, the pre-testing cells are placed into the chamber to begin pre-testing the chamber. In the preferred embodiment of the present invention, before beginning the drying process, the pre-tested cells are left in the chamber for about 10-15 minutes in order for the cells to become acclimated with the predetermined temperature and relative humidity in the chamber. Importantly and surprisingly, according to the methods of the present invention, restricted ranges of temperature and relative humidity provide optimized results for best chromosome spreading consistency. FIGS. 2a, 2b, and 2c show testing conducted over a period of ten weeks to determined optimal chromosomal spread consistency at relative humidity ranges from about 34.5% to about 37.5%, and at temperature ranges from about 30.4° C. to about 32.2° C. The results of the ten week testing are shown in greater detail in FIG. 1, which indicates that optimal chromosome spread consistency occurs when the air flow is fixed, the temperature is maintained between about 31.5-32.0° C. and the relative humidity is about 36%. By tightening or restricting the range for relative humidity and temperature, optimum chromosome spreading consistency occurs because the acetic acid and methanol as chemicals behave differently if the range is too broad, negatively impacting chromosome spreading consistency.

A range for humidity between about 40 and about 60 percent within the closed room is preferred, with the temperature being about 72° F.F, or 22.2° C. The cells are then placed in the cytogenetic chamber and allowed to adjust. The cells in the fixative acclimate to the new humidity and temperature therein. After about 10-15 minutes have passed, the vacuum pump in the chamber should be activated in order to aspirate the fixative. In the preferred embodiment, aspiration requires about 3 seconds. While the fixative is aspirating a pipette may be used to make a sweeping motion along the circumference of the support to remove all of the fixative. Pipetting is performed to remove all of the fixative to ensure that there is substantially no water present. A slip is placed under the air flow before opening the cells. In the preferred embodiment, once the fixative agent is removed, the pre-testing cells are dried. The pre-testing cells are dried for about 2 minutes. It is important for the present invention to achieve optimum conditions for the cells to open in order for the metaphase chromosomes to spread for each of the tissue types, so that special banding techniques and high resolution chromosomal analysis can be preformed. The morphology of the cells is "fuzzy" if the humidity range is too broad, and banding quality is diminished. Non-optimal humidity increases cytoplasm interfering with and/or adversely affecting the quality of chromosome preparation.

After the drying process is completed, the pre-testing cells are removed from the cytogenetic chamber for analysis. Ideally, the chromosomes should appear dark, thin and well spread. In the event the chromosomes are not dark and have not spread well, the cytogenetic chamber should be adjusted accordingly and additional pre-testing cells should be dried at the newly calibrated conditions. The present invention has found that chromosomal spreading is more readily affected by temperature. The temperature is adjusted to improve chromosome spreading. According to methods of the present invention, based upon relative humidity, temperature and air flow variation, and more particularly, based upon restricted ranges for them, especially for relative humidity, the chromosome spreading and consistency of chromosome spreading are improved. Thus, the present invention methods improve not only the quality of chromosome spreading, but the consistency of it as well. The most consistent method of chromosome spreading is provided with restricted relative humidity ranges as illustrated in the figures, even for varied temperature and air flows.

These methods of the present invention provide consistent chromosome spreading and obtain non-fuzzy, well-spread, and crisply banded high resolution metaphase chromosome spreads. The metaphase chromosome analysis is the cell stage, as set forth hereinabove. A growth phase wherein there is replication of the DNA and chromosomes provides for division and growth of the cells. First the cells condense to make a metaphase just before the cells divide or split. The chemical COLECEMID, which is an organic cytotoxin that impedes cell division at the metaphase stage is added to permit cell harvesting at the metaphase. Providing restricted humidity ranges provides optimized chromosome spreading consistency as set forth hereinabove.

The pre-testing step of the present invention reduces the risk of losing an entire biological sample in the event the environmental conditions of the chamber were not optimal as set. Consequently, the pre-testing step is both time and cost effective.

After the optimal drying and spreading conditions have been determined using the pre-testing cells, the reserved cells can be placed into the cytogenetic chamber for final treatment. In the preferred embodiment, the reserved cells are subjected to the same protocol as the pre-testing cells. The cytogenetic chamber should be set at the predetermined conditions based on the confirmed conditions during the pre-testing step. The reserved cells are placed into the chamber at the same predetermined conditions used for the pre-testing that yielded optimal spreading conditions. The reserved cells are first acclimated to the predetermined conditions before drying. In the preferred embodiment it requires about 10-15 minutes for the reserved cells to become acclimated to the conditions of the cytogenetic chamber. A vacuum pump is then activated to aspirate the fixative agent of the reserved cells, and thus removing the fixative from the reserved cell. In the preferred embodiment, aspirating the fixative requires about 3 seconds. Once all of the fixative is removed, the reserved cells are dried in the chamber. In the preferred embodiment, the drying process for the reserved cells requires about 2 minutes. After the reserved cells are dried, they are removed from the cytogenetic chamber and analyzed for cytogenetic studies. In the event the pre-testing step has demonstrated that it requires more or less time for aspiring the fixative agent or drying the biological sample, such times should be adjusted accordingly for the reserved cells.

By developing a method for obtaining optimal chromosome drying and spreading, the present invention facilitates the opening of cells to spread the metaphase chromosomes for each type of biological sample. The metaphase chromosomes are small and rounded, with very few overlapping chromosomes and consistent spreading. Additionally the chromosomes of the present invention are clear, intact, and are not over spread or scattered. Consequently, banding techniques at 550 bands and chromosomal analysis on high-resolution chromosomes can be achieved using the techniques of the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the following claims.

What is claimed is:

1. A method of drying chromosomes, the method comprising the steps of:
    a) preparing a biological sample for treatment by:
        i) obtaining a biological sample of cells for treatment;
        ii) transferring the sample of cells onto a support;
        iii) harvesting the sample of cells;
        iv) adding a fixative agent to the cells after the cells are harvested;
    b) providing a cytogenetic chamber capable of setting predetermined conditions;
    c) pre-testing the cytogenetic chamber by:
        i) setting the chamber to a predetermined condition based on the biological sample being treated;
        ii) placing a pre-testing portion of the cells with the fixative agent into the chamber and reserving a remainder of the cells;
        iii) allowing the pre-testing cells to become acclimated to the predetermined conditions before drying the pre-testing cells;
        iv) aspirating all of the fixative from the pre-testing cells;
        v) drying the pre-testing cells until spreading is optimized for consistency;
        vi) removing the pre-testing cells and analyzing for optimal chromosome spreading for consistency;
    d) placing the reserved cells into the chamber at the same predetermined conditions used for the pre-testing, allowing the reserved cells to become acclimated to the predetermined conditions before drying the reserved cells, aspirating the fixative from the reserved cells, drying the reserved cells, and analyzing the reserved cells for optimal chromosomal spreading.

2. The method of claim 1, wherein the predetermined condition of the chamber has a temperature of about 30.0-32.0° C. and a relative humidity of about 35-37%.

3. The method of claim 2, wherein the biological sample comprises an amnioctye, an early amniocyte, and a chorionic villus sampling (CVS).

4. The method of claim 1, wherein the predetermined condition of the chamber has a temperature of about 31.0-33.0° C. and a relative humidity of about 36-38%.

5. The method of claim 4, wherein the biological sample comprises a product of conception or skin tissue.

6. The method of claim 1, wherein the predetermined condition of the chamber has a temperature of about 32° C. and a relative humidity of about 36-46%.

7. The method of claim 1, wherein the biological sample comprises a blood specimen, a bone marrow, and a tumor cell.

8. The method of claim 1, wherein the step of harvesting isolates the cells to form a solution of viable cells.

9. The method of claim 1, wherein the fixture agent comprises a 3:1 ratio of methanol to glacial acetic acid.

10. The method of claim 1, wherein the step of allowing the pre-testing cells to become acclimated to the predetermined conditions take about 15 minutes.

11. The method of claim 1, wherein the step of aspirating the fixative from the pre-testing cells requires about 3 seconds.

12. The method of claim 1, wherein the step of drying the pre-testing cells requires about 2 minutes.

13. A method of drying chromosomes, the method comprising the steps of:
    a) preparing a biological sample for treatment by:
        i) obtaining a biological sample of cells for treatment, wherein the biological sample comprises an amnioctye, an early amniocyte, and a chorionic villus sampling (CVS);
        ii) transferring the sample of cells onto a support;
        iii) harvesting the sample of cells;
        iv) adding a fixative agent to the cells after the cells are harvested;
    b) providing a cytogenetic chamber capable of setting predetermined conditions;
    c) pre-testing the cytogenetic chamber by:
        i) setting the chamber to a predetermined condition, wherein the predetermined condition is a temperature of about 30.0-32.0° C. and a relative humidity of about 35-37%;
        ii) placing a pre-testing portion of the cells with the fixative agent into the chamber and reserving a remainder of the cells;

iii) allowing the pre-testing cells to become acclimated to the predetermined conditions before drying the pre-testing cells;
iv) aspirating all of the fixative from the pre-testing cells;
v) drying the pre-testing cells until spreading is optimized for consistency;
vi) removing the pre-testing cells and analyzing for optimal chromosome spreading for consistency;

d) placing the reserved cells into the chamber at the same predetermined conditions used for the pre-testing, allowing the reserved cells to become acclimated to the predetermined conditions before drying the reserved cells, aspirating the fixative from the reserved cells, drying the reserved cells, and analyzing the reserved cells for optimal chromosomal spreading.

14. A method of drying chromosomes, the method comprising the steps of:
a) preparing a biological sample for treatment by:
i) obtaining a biological sample of cells for treatment, wherein the biological sample comprises a product of conception and skin tissue;
ii) transferring the sample of cells onto a support;
iii) harvesting the sample of cells;
iv) adding a fixative agent to the cells after the cells are harvested;
b) providing a cytogenetic chamber capable of setting predetermined conditions;
c) pre-testing the cytogenetic chamber by:
i) setting the chamber to a predetermined condition, wherein the predetermined condition is a temperature of about 31.0-33.0° C. and a relative humidity of about 36-38%;
ii) placing a pre-testing portion of the cells with the fixative agent into the chamber and reserving a remainder of the cells;
iii) allowing the pre-testing cells to become acclimated to the predetermined conditions before drying the pre-testing cells;
iv) aspirating all of the fixative from the pre-testing cells;
v) drying the pre-testing cells until spreading is optimized for consistency;
vi) removing the pre-testing cells and analyzing for optimal chromosome spreading for consistency;
d) placing the reserved cells into the chamber at the same predetermined conditions used for the pre-testing, allowing the reserved cells to become acclimated to the predetermined conditions before drying the reserved cells, aspirating the fixative from the reserved cells, drying the reserved cells, and analyzing the reserved cells for optimal chromosomal spreading.

15. A method of drying chromosomes, the method comprising the steps of:
a) preparing a biological sample for treatment by:
i) obtaining a biological sample of cells for treatment, wherein the biological sample comprises a blood specimen, a bone marrow, and a tumor cell;
ii) transferring the sample of cells onto a support;
iii) harvesting the sample of cells;
iv) adding a fixative agent to the cells after the cells are harvested;
b) providing a cytogenetic chamber capable of setting predetermined conditions;
c) pre-testing the cytogenetic chamber by:
i) setting the chamber to a predetermined condition, wherein the predetermined condition is a temperature of about 32° C. and a relative humidity of about 36-46%;
ii) placing a pre-testing portion of the cells with the fixative agent into the chamber and reserving a remainder of the cells;
iii) allowing the pre-testing cells to become acclimated to the predetermined conditions before drying the pre-testing cells;
iv) aspirating all of the fixative from the pre-testing cells;
v) drying the pre-testing cells until spreading is optimized for consistency;
vi) removing the pre-testing cells and analyzing for optimal chromosome spreading for consistency;
d) placing the reserved cells into the chamber at the same predetermined conditions used for the pre-testing, allowing the reserved cells to become acclimated to the predetermined conditions before drying the reserved cells, aspirating the fixative from the reserved cells, drying the reserved cells, and analyzing the reserved cells for optimal chromosomal spreading.

* * * * *

UNITED STATES PATENT AND TRADEMARK OFFICE
CERTIFICATE OF CORRECTION

| | | |
|---|---|---|
| PATENT NO. | : 8,057,995 B2 | |
| APPLICATION NO. | : 11/545827 | |
| DATED | : November 15, 2011 | |
| INVENTOR(S) | : Philip D. Buchanan | |

It is certified that error appears in the above-identified patent and that said Letters Patent is hereby corrected as shown below:

In Claim 2, Column 8, line 21, delete "." after "30.0-32.0°C"

2. The method of claim 1, wherein the predetermined condition of the chamber has a temperature of about 30.0-32.0°C[[.]] and a relative humidity of about 35-37%.

In Claim 3, Column 8, line 23, delete "amnioctye" from before ", and early" and replace with "amniocyte"

3. The method of claim 2, wherein the biological sample comprises an amnioc[[t]]yte, an early amniocyte, and a chorionic villus sampling (CVS).

In Claim 4, Column 8, line 27, delete "." after "31.0-33.0°C"

4. The method of claim 1, wherein the predetermined condition of the chamber has a temperature of about 31.0-33.0°C[[.]] and a relative humidity of about 36-38%.

In Claim 6, Column 8, line 31, delete "." after "about 32.0°C"

6. The method of claim 1, wherein the predetermined condition of the chamber has a temperature of about 32° C[[.]] and a relative humidity of about 36-46%.

In Claim 8, Column 8, line 36, insert --from-- after "harvesting isolates"

8. The method of claim 1, wherein the step of harvesting isolates from the cells to form a solution of viable cells.

Signed and Sealed this
Thirteenth Day of March, 2012

David J. Kappos
*Director of the United States Patent and Trademark Office*

CERTIFICATE OF CORRECTION (continued)

U.S. Pat. No. 8,057,995 B2

In Claim 10, Column 8, line 41, delete "take" and insert --takes--

10. The method of claim 1, wherein the step of allowing the pre-testing cells to become acclimated to the predetermined conditions [[take]] takes about 15 minutes.

In Claim 13, Subsection a) i), Column 8, line, 51-52, delete "amnioctye" from before ", and early" and replace with "amniocyte"

i) obtaining a biological sample of cells for treatment, wherein the biological sample comprises an amnioc[[t]]yte, an early amniocyte, and a chorionic villus sampling (CVS);

In Claim 13 c) i), Column 8, line 63, delete "." after "30.0-32.0° C"

i) setting the chamber to a predetermined condition, wherein the predetermined condition is a temperature of about 30.0-32.0° C[[.]] and a relative humidity of about 35-37%;

In Claim 14, Subsection c) i), Column 9, line 32, delete "." after "31.0-33.0° C"

i) setting the chamber to a predetermined condition, wherein the predetermined condition is a temperature of about 31.0-33.0° C[[.]] and a relative humidity of about 35-37%;

In Claim 15, Subsection c) i), Column 10, line 23, delete "." after "about 32.0° C"

i) setting the chamber to a predetermined condition, wherein the predetermined condition is a temperature of about 32° C[[.]] and a relative humidity of about 36-46%;